United States Patent [19]

Hartl

[11] Patent Number: 5,180,293
[45] Date of Patent: Jan. 19, 1993

[54] THERMOELECTRICALLY COOLED PUMPING SYSTEM

[75] Inventor: Hans-georg Hartl, Wilmington, Del.
[73] Assignee: Hewlett-Packard Company, Palo Alto, Calif.
[21] Appl. No.: 855,185
[22] Filed: Mar. 20, 1992
[51] Int. Cl.⁵ .............................................. F04B 39/06
[52] U.S. Cl. ..................................... 417/366; 417/372
[58] Field of Search ...................... 417/228, 366, 372; 62/3.2, 505

[56] References Cited

U.S. PATENT DOCUMENTS

| | | | |
|---|---|---|---|
| 2,772,831 | 12/1956 | Cotter | 417/228 |
| 3,744,935 | 7/1973 | Magni | 417/366 |
| 4,825,667 | 5/1989 | Benedict et al. | 62/3.2 |

FOREIGN PATENT DOCUMENTS 0112965 6/1966 Netherlands ............................ 62/3.2

Primary Examiner—Richard A. Bertsch
Assistant Examiner—Charles Freay
Attorney, Agent, or Firm—Richard F. Schuette

[57] ABSTRACT

A method and apparatus for accurately regulating the compressibility of a compressible fluid in a thermoelectrically cooled pumping system having a first heat exchanger for precooling the compressible fluid utilizing cooled fluid which has been outputted from the pump and a second heat exchanger, coupled to the pumphead which incorporates thermoelectric cooling elements, for cooling the compressible fluid immediately prior to being pumped.

9 Claims, 6 Drawing Sheets

THERMOELECTRICALLY COOLED PUMPING SYSTEM

BACKGROUND OF THE INVENTION

In a pumping system for highly compressible fluids (for example, $CO_2$), an important feature is the ability to keep the pump head of the pumping apparatus and the pumping fluid at a low temperature to reduce the compressibility of the pumping fluid just prior to pumping. Additionally, it is important to stabilize fluid flow by maintaining the pumping fluid at a constant temperature prior to pumping. Currently, there is intense interest in using near-critical and supercritical fluids at elevated pressures as solvents in extraction systems and in chromatographic systems. Often the solvents of interest exist as highly compressible fluids at ambient pressures and temperatures from 15–40 degrees centigrade. At ambient conditions, fluids such as carbon dioxide, ethylene, ethane and sulfur hexafluoride have high vapor pressures which significantly exceed 1 atmosphere. However, those pressures are not sufficiently high for extraction and chromatographic applications at or near supercritical conditions. Therefore, liquid state fluids must be supplied to some type of pumping system to meet pressure and flow requirements of the high pressure processes downstream of the pumping system.

The compressible fluids used for extraction or chromatography are typically supplied in the liquid phase in pressurized tanks. These tanks are not completely filled with liquid and pressure stabilizes at the vapor pressure of the liquid at the current tank ambient temperature A pressure drop in the liquid generally occurs as the liquid is supplied to the pump. Flashing may occur where fluid in the liquid phase is mixed with fluid in the gas phase resulting in a two phase fluid mixture which is more compressible than the original single phase fluid. Therefore, the efficiency and metering accuracy of a solvent delivery system can be greatly enhanced by decreasing the compressibility and hence increasing the bulk modulus of the fluid by precisely maintaining the pumping fluid at sub-ambient conditions/temperatures. It is also important to keep the temperature as stable as possible to improve the accuracy of the pumping system.

Most of the current solvent delivery systems utilize syringe pumps with pumping cylinders having large compression ratios A major drawback of such systems is the need to interrupt the chromatographic process to refill the cylinder once it is empty.

In order to decrease the compressibility of the fluid and thereby decrease the corresponding compression ratio so that liquid-type pumps with continuous flow capability can be used, it is necessary to pre-cool the compressible fluid prior to entry into the pump. Heat exchangers and cooling baths are typically employed for this purpose. Furthermore, it is also necessary to cool the pump head separately to keep the compressibility of the fluid constant at a low value during the pumping process.

A typical prior art pumping system is illustrated in FIG. 1 in which pre-cooling of the pumping fluid 1 to sub-ambient temperatures has been accomplished by feeding the pumping fluid through a heat exchanger 2 of a pre-cooler 4. The pre-cooler 4 is placed in a recirculating bath 5 which contains a cooled liquid having a regulated temperature measured by a thermocouple 6. The cooled liquid is also circulated to a pump head 7 by a recirculating pump 8 to keep it at sub-ambient temperatures. FIG. 2 is a more detailed view of the pump head and illustrates problems associated with cooling the pump head and the pumping fluid separately.

Another prior art technique for cooling a pump head is disclosed in co-pending patent application Ser. No. 07/662,687 entitled "Cooled Pumping System" in which a single source of cryogenic fluid is employed for cooling a pump head, having a much higher thermal conductivity than the pump body, simultaneously with the pumping fluid just prior to pumping.

Thermoelectric devices which utilize the Peltier effect have come into widespread use as solid-state heating and cooling elements. However, the amount of heat such devices are capable of removing is limited by the inherent ability to transfer heat from the outer surfaces of the devices. Additionally, the efficiency of such devices degrades rapidly with the temperature differential between the surface being cooled and the surface of the heat exchanger. Prior to the invention, it was not possible to effectively thermoelectrically cool a liquid such as $CO_2$ so that it can by pumped at sub-ambient conditions.

It is desirable to eliminate the need for either recirculating baths or cryogenic cooling. Both require constant maintenance and in the case of cryogenic cooling, lots of cryogenic cooling agent, usually $CO_2$, which comes in bulky tanks.

SUMMARY OF THE INVENTION

It is therefore a primary object of this invention to provide a method and apparatus for pumping fluids at sub-ambient and constant temperatures such that accurate regulation of the compressibility can be obtained as well as stabilization of the pumping fluid. It is an additional object of the invention to provide for such sub-ambient and constant temperature pumping without utilizing cryogenic or recirculating bath cooling.

In accordance to the above, the invention provides for a thermoelectrically cooled pumping system which does not employ recirculating bath or cryogenic cooling. Since the temperature of the pumping fluid after pumping is not critical to stabilization of the pumping fluid, the invention utilizes the relatively cool pumped fluid exiting the pump head to precool the fluid entering the pump head to be pumped. The invention includes a first counterflow heat exchanger in which the pumping fluid outputted from the pump is utilized to precool the fluid prior to pumping, and a second heat exchanger coupled to the pump head inlet to further cool the compressible fluid immediately prior to being pumped. The counterflow heat exchanger reduces the amount of energy required to bring the temperature of the pumping fluid to sub-ambient conditions such that thermoelectric cooling elements which do not have a very large thermal transfer capacity, can be employed to complete the cooling prior to being inputted into the pump head.

The foregoing and other object, features and advantages of the invention will be apparent from the following more particular description of preferred embodiments of the invention as illustrated in the accompanying drawings.

DESCRIPTION OF THE PREFERRED EMBODIMENT

Figure 1:
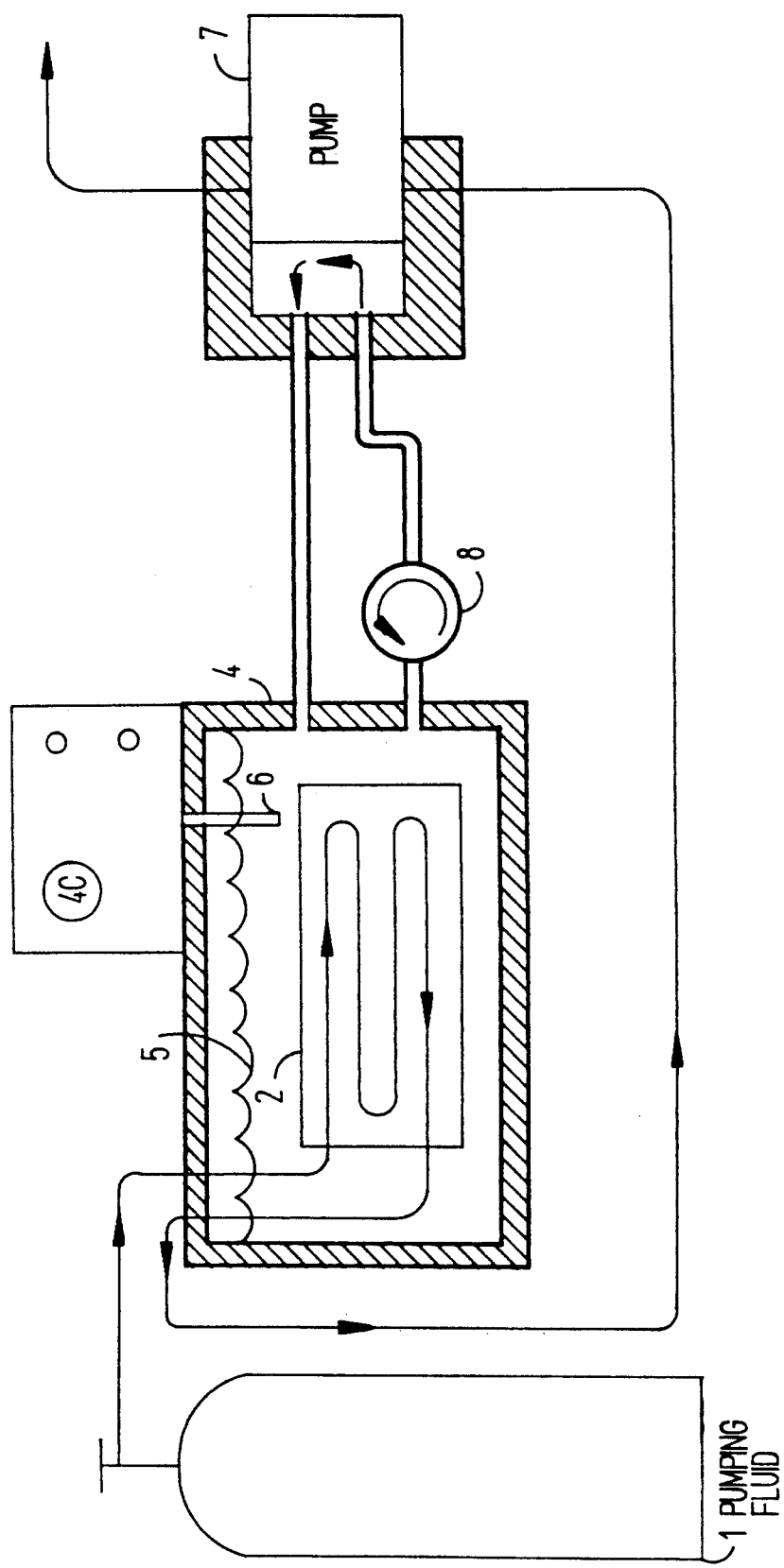
FIG. 1 illustrates the prior art fluid pumping system having two zones cooled by a recirculating bath.
Figure 2:
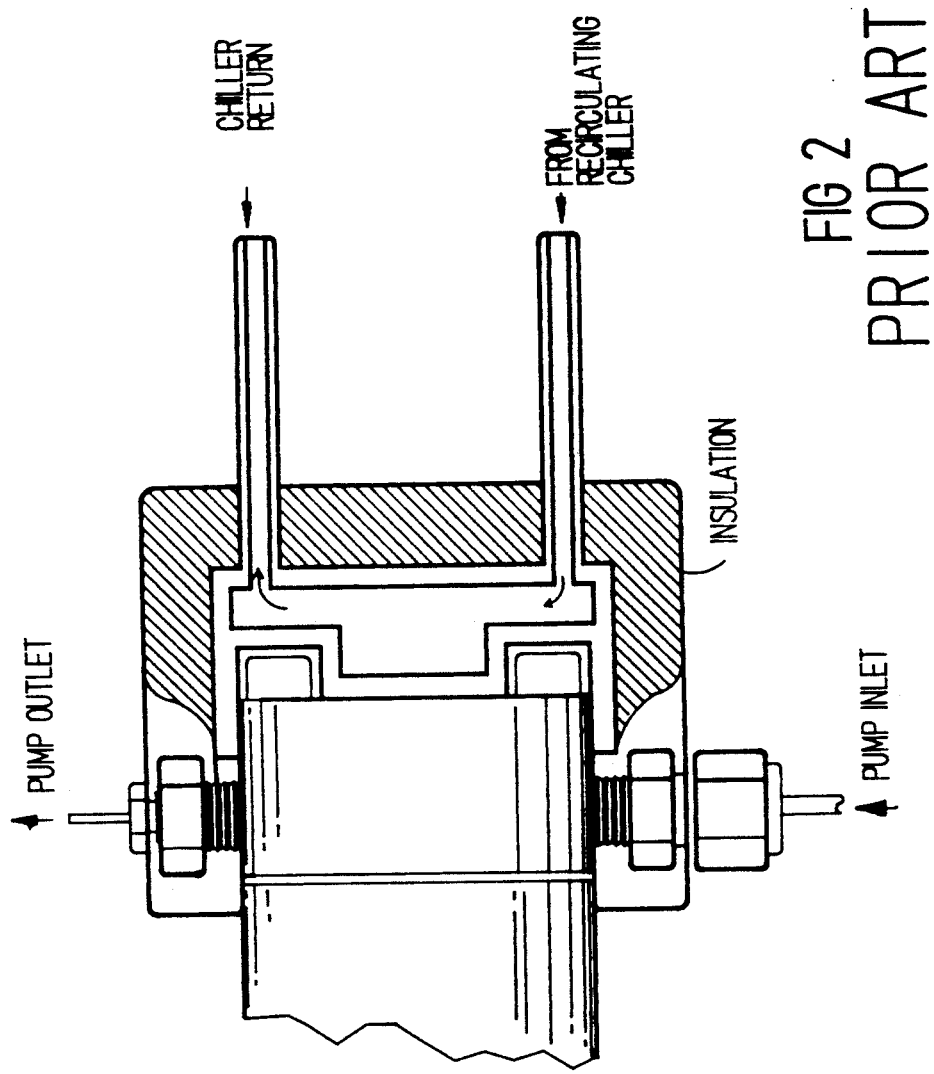
FIG. 2 illustrates the pump head of the prior art pumping system of FIG. 1.
Figure 3:
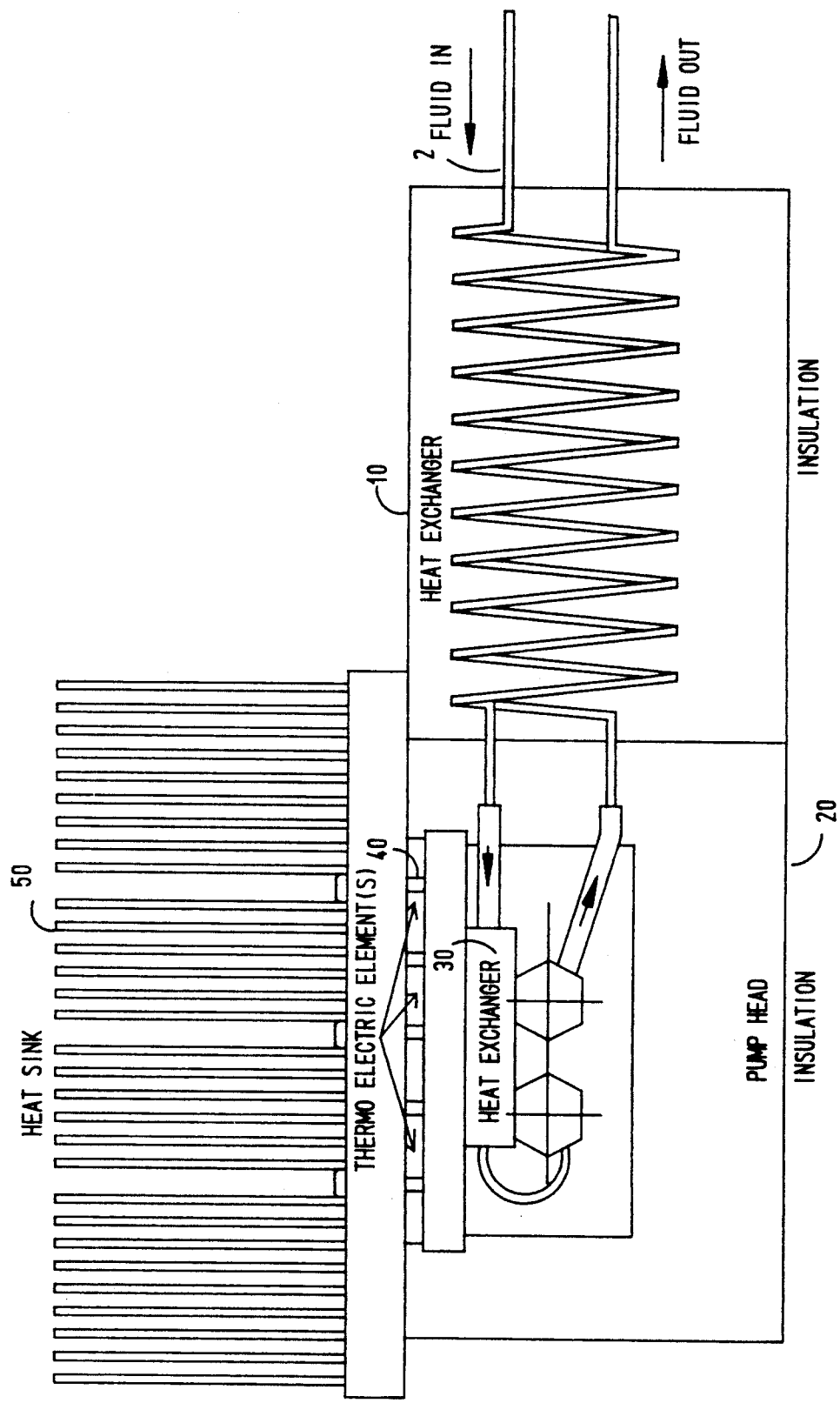
FIG. 3 illustrates the preferred embodiment of the invention employing a counterflow heat exchanger and a thermoelectrically cooled pump head.

In the preferred embodiment of the thermoelectrically cooled SFC pumping system, a high pressure pump typically used in liquid chromatography is modified for low temperature operation. As set forth in FIG. 3, the pump includes a pump head 20 and a pair of cylinders which are thermally isolated from the body of the pump. Two heat exchangers are hydraulically coupled to the pump head to ensure that the pumping fluid is maintained at approximately 4 degrees centigrade, thereby decreasing the compressibility of the fluid. The first heat exchanger 10 is hydraulically coupled to the pump head. Since the temperature of the pumping fluid after pumping does not effect the performance of the pumping system, a counterflow heat exchanger can be employed for precooling the incoming by utilizing the relatively cool fluid being pumped from the pump head 20. The second heat exchanger 30 is coupled to the pump head 20 such that pumping fluid exiting this heat exchanger is inputted directly into the first cylinder of the pump head 20. Thermoelectric elements 40 are coupled on one side to the second heat exchanger 30 and on the other side to the heat sink 50. The thermoelectric elements 40 pull heat from the pump head such that it can be dissipated by the heat sink 50. These elements 40 have the ability to generate a temperature differential of approximately 70 degrees centigrade between their hot and cold sides. However, the total amount of heat they are capable of removing is inversely related to the temperature differential across them.

Figure 4:
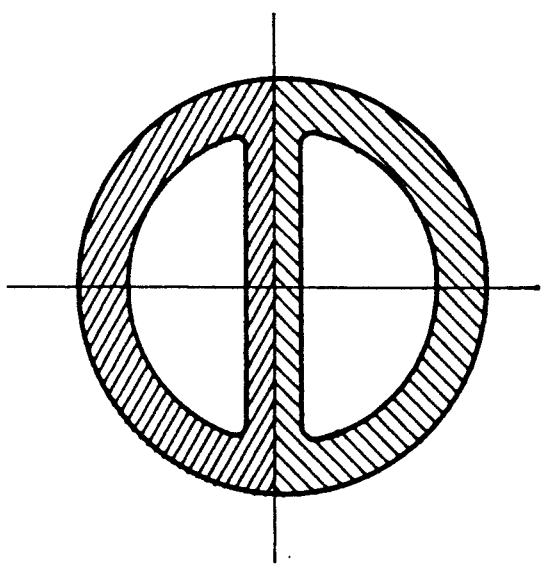
FIG. 4 illustrates the preferred embodiment of the counterflow heat exchanger having double "D" construction.
Figure 5:
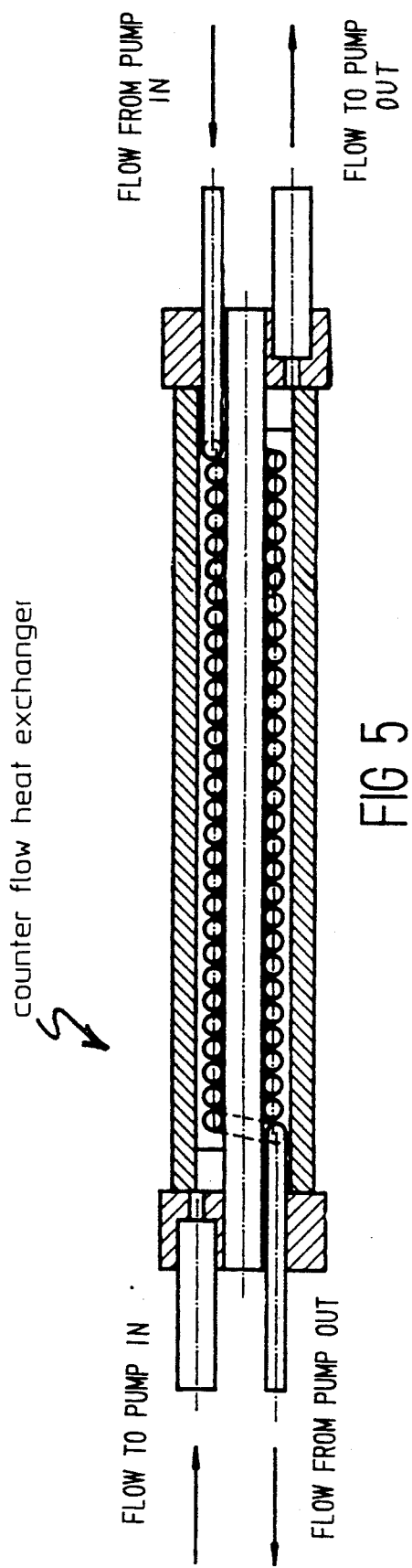
FIG. 5 illustrates a porous metal heat exchanger as utilized in the preferred embodiment of the invention.

The compressibility of the pumping fluid is sufficiently reduced when the temperature of the fluid is maintained at approximately 4 degrees centigrade. Thus, maintaining the temperature of the fluid to be pumped near this temperature will enable the requisite accurate metering of the pumping fluid in terms of ml/min. Since the temperature of the fluid after it exits the pump is not critical, the counterflow heat exchanger 10 can utilize the cooling power of the fluid which exits the pump to precool the fluid to be pumped. FIG. 4 illustrates a preferred embodiment of this heat exchanger in which two "D" shaped tubes are joined along their longitudinal axis. By joining them along their flat sides, the contact area and ability to transfer heat is maximized. FIG. 5 illustrates an alternative embodiment in which a coil of relatively small diameter tube is placed inside a larger diameter tube. Fluid flows in opposite directions through these two tubes thereby providing an effective means of pre-cooling.

Figure 6:
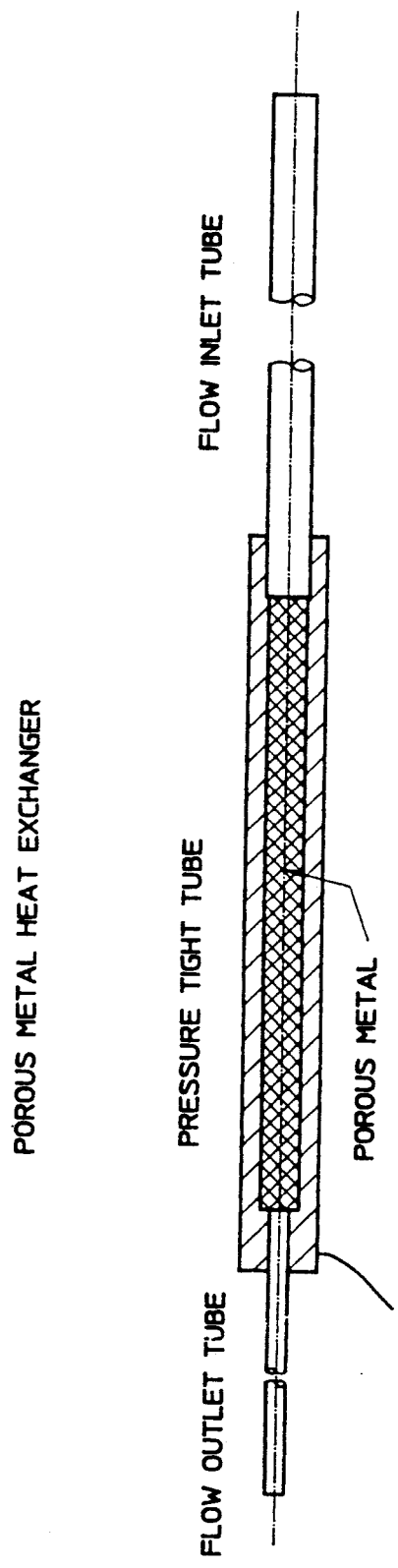
FIG. 6 illustrates an alternative preferred embodiment of the counterflow heat exchanger without double "D" construction.

FIG. 6 illustrates the preferred embodiment of the second heat exchanger 30 in which thermally conductive and chemically inert porous metal media is enclosed within a solid metal tube (for example, pure nickel). The porous metal fills approximately 50% of the tube volume which leaves a large number of very small flow paths and maximizes the surface area to volume ratio. Pre-cooled pumping fluid exits the counterflow heat exchanger and flows through the porous metal frit such that heat is exchanged between the fluid in the flowpath and the heat exchanger.

As previously set forth, thermoelectric elements 40 pull heat out of the pump head such that it can be dissipated by the heat sink 50. If it were not for the precooling, the thermoelectric elements could not effectively cool the pump head as the total amount of heat they are capable of removing is inversely related to the differential between the temperature of the pumping fluid and the ambient air temperature. The invention utilizes the relatively cool fluid exiting the pump as a means for reducing the amount of energy to be removed at the pump head. Thermoelectric cooling is also advantageous in that it enables precise controlling of pump head temperature and does not require recirculating baths or a cryogenic fluid which necessitates high maintenance.

Although best results are obtained by the foregoing method and apparatus for a thermoelectrically cooled pumping system, changes and modification of the invention, as set forth in the specifically described embodiments, can be carried out without departing from the scope of the invention which is intended to be limited only by the scope of the appended claims.

We claim

1. A pumping system for pumping fluids at sub-ambient temperatures, comprising:
    a pump head having an inlet and an outlet such that fluid flowing into the pump head through the inlet is compressed and outputted through said outlet; and
    pump head heat exchanger means having an inlet and an outlet, wherein, said outlet is coupled to said pump head inlet; and
    counter flow heat exchanger means having a first and second inlet and a first and second outlet, said first outlet being coupled to pump head heat exchanger inlet and said second inlet being coupled to said pump head outlet, wherein, the fluid to be pumped enters said first counter flow heat exchanger inlet and exits said second counter flow heat exchanger outlet, wherein, said fluid entering said second counter flow heat exchanger input is in thermal contact with fluid entering said first counter flow heat exchanger input; and
    thermoelectric elements, coupled to said pump head heat exchanger means for dissipating heat from said pump head and cooling the pumping fluid;.- wherein, said cooled pumping fluid exiting the pump enters said counterflow heat exchanger and precools said pumping fluid to sub-ambient temperatures prior to pumping.

2. The pumping system of claim 1, wherein said pump head heat exchanger means is integral to said pump head.

3. The pumping system of claim 2, said pump head heat exchanger means further comprising a solid metal tube partially filled with a porous metal media such that there is a large number of small flow paths to maximize the surface are to volume ratio and heat transfer.

4. The pumping system of claim 1, said pump head heat exchanger means further comprising two tubes have a "D" cross section which are joined along their respective flat longitudinal axis.

5. The pumping system of claim 1, said pump head heat exchanger means further comprising a coil of tubing placed inside a second tube.

6. A method for pumping fluids at sub-ambient temperatures comprising the method steps of:

directing a pumping fluid through a counter-flow heat exchanger prior to pumping by a pump head, wherein, said pump head has an inlet for fluid to be pumped and an outlet for pumped fluid, and wherein, said outlet is coupled to said counter flow heat exchanger such that said pumped fluid precools said pumping fluid prior to being pumped, thermoelectrically cooling a pump head heat exchanger having an inlet attached to said counterflow heat exchanger and an outlet coupled to said pump head inlet, such that said precooled pumping fluid is cooled to sub-ambient temperatures prior to being pumped.

7. The method for pumping fluids at sub-ambient temperatures as claimed in claim 6, wherein said counter flow heat exchanger comprises two "D" shaped tubes joined along their respective flat longitudinal axis such that fluid to be pumped and pumped fluid exiting the pump head flows in opposite directions through said tubes.

8. The method for pumping fluids at sub-ambient temperatures as claimed in claim 6, wherein said counterflow heat exchanger comprises a coil of tubing placed inside a second tube.

9. The method for pumping fluids at sub-ambient temperatures as claimed in claim 6, wherein, said pump head heat exchanger includes a porous metal media.

* * * * *